United States Patent [19]

Nakano et al.

[11] Patent Number: 5,622,942
[45] Date of Patent: Apr. 22, 1997

[54] PERCUTANEOUS ABSORPTIVE ANESTHETIC

[75] Inventors: Masahiro Nakano; Motohiro Mishima, both of Kumamoto; Tatsuhiko Kano, Yatsushiro-gun; Nobuyuki Nagata, Kawasaki, all of Japan

[73] Assignee: Minophagen Pharmaceutical Company, Tokyo, Japan

[21] Appl. No.: 142,332

[22] PCT Filed: Apr. 24, 1992

[86] PCT No.: PCT/JP92/00543

§ 371 Date: Nov. 22, 1993

§ 102(e) Date: Nov. 22, 1993

[51] Int. Cl.$^6$ ................................. A61K 31/56
[52] U.S. Cl. ................ 514/171; 514/172; 514/177; 514/180; 514/181; 514/182
[58] Field of Search ..................... 514/171, 172, 514/177, 180, 181, 182

[56] References Cited

U.S. PATENT DOCUMENTS 4,772,470 9/1988 Inoue et al. .......................... 424/435
5,260,066 11/1993 Wood et al. ........................... 424/447

FOREIGN PATENT DOCUMENTS 3-99023A 4/1991 Japan .

OTHER PUBLICATIONS

CA 101:A8855 "Sipos Alcoholic Potentating agent for skin penetration of topical drugs" Corresponding to Australian Patent AU 534455, Feb. 2, 1984. Abstract only.
Medline Abstract 89351398 Touitou et al, "Glycyrrhizin gel as vehicle for idoxuridine topical preparation" Drug Des deliv Nov. 1988 3(3) 267–72, Abstract only.

"Relief of Experimentally Induced Pruritus with a Novel Eutectic Mixture of Local Anaesthetic Agents", D. Shuttleworth, S. Hill, R. Marks and D.M. Connelly, British Journal of Dermatology, 119:535–540 (1988).
"Prilocaine–Induced Methemoglobinemia in a Newborn Infant", Peter. G. Duncan, M.D., F.R.C.P. (C). and Nathan Kobrinsky, M.F., F.R.C.P. (C), Clinical Reports, Anesthesiology, 59:75–76 (1983).
"Concentration–Response Analysis of Percutaneous Local Anaesthetic Formulations", A.D. Woolfson, D.F. McCafferty, K.H. McClelland and V. Boston, British Journal of Anaesthesia, 61:589–592 (1988).
"In Vivo Assessment of Percutaneous Local Anaesthetic Preparations", D.F. McCafferty, A.D. Woolfson and V. Boston, Br. F. Anaesth. 62:17–21 (1989).
"EMLA: A New Topical Anesthetic", Lennart Juhlin, M.D., Hans Evers, D.D.S., Ph.D. (Hon.), Adv. Dermatol 5:75–92 (1990).
"A Lidocaine–Prilocaine Cream for Superficial Skin Surgery and Painful Lesions", Lennart Juhlin, Hans Evers and Fredrik Broberg, Acta Dermatovener (Stockholm), Short Reports, 60:544–546 (1980).
Elka Touitou et al, "Glycyrrhizin Gel as Vehicle for Idoxuridine Topical Preparation: Skin Permeation Behavior", Drug Design and Delivery, 1988 vol. 3, pp. 267–272.

*Primary Examiner*—Marianne M. Cintins
*Assistant Examiner*—Keith MacMillan
*Attorney, Agent, or Firm*—Knobbe, Matens, Olson & Bear

[57] ABSTRACT

A percutaneous absorptive anesthetic is provided, wherein said anesthetic is formed by mixing a base agent of said anesthetic with one or two type of mixtures which has/have been selected from the groups, for example made of glycyrrhizin, glycyrrhetic acid, glycyrrhetic acid derivatives glycyrrhetic acid 3β-monohemisuccinate, glycyrrhetic acid 3β-monohemisuccinate, 18β-olean-12-ene-3β, 30-dihemiphthalate, 18β-olean-9, (11)12-diene-3β, 30-diol-dihemiphthalate, olean-11,13(18)-diene-3β, 30-diol-dihemiphthalate or their pharmaceutically allowable salt.

8 Claims, 1 Drawing Sheet

PERCUTANEOUS ABSORPTIVE ANESTHETIC

This application is a 371 of PCT JP 92/00543, filed Apr. 24, 1992.

TECHNICAL FIELD

The present invention relates to a percutaneous absorptive anesthetic in which a local anesthetic is mixed with an absorption-promoting substance.

BACKGROUND ART

There have been proposed various medicines in the prior art which may be percutaneously absorbed and is effective when applied on the topical site in the human body. These medicines which are intended for topical anesthesia include, for example, an injection, and a liquid, jelly and spray, etc. for use as a surface anesthetic.

However, the latter surface anesthetic is known to provide a remarkable topical anesthetic effect against the mucous membrane of esophagus, stomach and mouth etc. but it is quite ineffective against the topical anesthesia of the skin.

Recently, in the field of anesthesia, the need of pain removal has become a matter of concern when a relatively thick needle is pierced through the skin in such a case where the vena must be punctured to get an access to the vessel, or when the epidural anesthesia and spinal anesthesia etc. must be effectuated. That is, an anesthetic such as lidocaine hydrochloride and procaine hydrochloride etc. have traditionally been dosed to the patient through the syringe, but such procedure cannot avoid causing pain to the patient during a dosing procedure.

With the above-described as a background, the inventor et al of the present patent application has been engaged in the developmental work to provide means which allow lidocaine etc. to be absorbed percutaneously, and tried various substances in order to shorten the time needed for the topical anesthesia to take effect, through an improved percutaneous absorptive effect. As a result, the inventor has found that glycyrrhizin and glycyrrhetic acid, and their derivatives have a remarkable percutaneous absorption improving effect, and thus the present invention has been achieved.

DISCLOSURE OF THE INVENTION

The percutaneous absorptive anesthetic in accordance with the present invention consists of one or more types of mixture which has/have been selected from the group made of compounds as listed below, and an anesthetic.

Typical compounds may be those to be represented by the general formula given below;

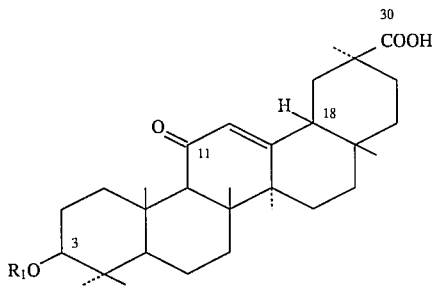

[provided that $R_1$ represents HOOC—. —H,

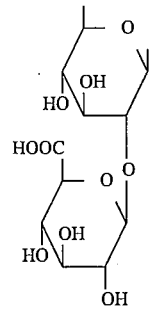

—OCCH$_2$CH$_2$COOH, or a compound to be represented by

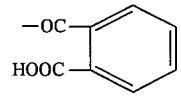

In addition, a compound that has a pharmaceutically allowable salt as its effective ingredient, its derivative of the glycyrrhetic acid represented by the following formula, and its pharmaceutically allowable salt.

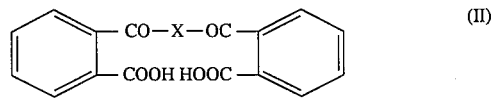

[provided that X represents a remaining radical of 18β-olean-12-ene-3 β, 30-diol, 18β-olean-9, (11)12-diene-3 β, 30-diol, or olean-11,13(18)-diene-3β and 30-diol]

Among the compounds which may belong to those represented by the above general formulas (I) and (II), the following substances can be listed.

(1) Glycyrrhizin
(2) Glycyrrhetic acid
(3) Glycyrrhetic acid 3β-monohemisuccinate
(4) Glycyrrhetic acid 3β-monohemiphthalate
(5) 18β-olean-12-ene-3 β, 30-diol-3 β, 30-dihemiphthalate
(6) 18β-olean-9(11), 12-diene-3 β, 30-diol-3 β, 30-dihemiphthalate
(7) Olean-11,13(18)-diene-3 β, 30-diol-3 β, 30-dihemiphthalate These compounds (1)–(7) are cited hereinbelow as compounds 1–7.

Such compounds as lidocaine, bupivacaine, tetracaine, prilocaine, etc. may be suggested for selection as an anesthetic.

The skeleton of the above-described compound is formed from an active ingredient which is contained in a glycyrrhiza, and displays a remarkable percutaneous absorption improving effect, whereas its side effect against the skin is extremely negligible. Consequently, the compound of the present invention may serve to substantially reduce the time needed for the anesthetic such as lidocaine, bupivacaine, tetracaine, prilocaine, etc. to take effect causing a skin anesthesia after being applied.

Besides, it may be well expected for the compound to absorb various other medicines used on the topical site more easily.

The disodium salt of the compounds 3–7 may be produced in the procedure to be described hereinbelow.

(1) To produce the compound 3, a succinic acid anhydride is added to glycyrrhetic acid.
(2) To produce the compound 4, a phthalic acid anhydride is added to glycyrrhetic acid.
(3) To produce the compound 5, a phthalic acid anhydride is added to 18β-olean-12-ene-3 β, 30-diol.

(4) To produce the compound 6, a phthalic acid anhydride is added to 18β-olean-9, (11)12-diene-3 β, 30-diol.

(5) To produce the compound 7, a phthalic acid anhydride is added to olean-11,13(18)-diene-3 β, 30-diol, and the compound may be synthesized in the organic solvent utilizing a weakly or strongly basic catalyst. In this case, pyridine, chloroform, methanol and ethanol etc. are used as an organic solvent, whereas diethylamine and triethylamine etc. are used as a weakly basic catalyst, and 4-dimethylaminopyridine etc. is used as a strongly basic catalyst.

This percutaneous absorptive anesthetic should preferably contain 0.1–20 weight percent of one or more type of mixtures which has/have been selected from the above group of compounds, and 0.1–50 weight percent of above anesthetic.

The compounds represented by the above general formulas (I) and (II) are mixed with the anesthetic with no alteration or in the form of alkali-added salt which may be applicable for the pharmaceutical purpose, and thereby forming it in the form of ointment, tape-coated medicine or poultice which can be applied as percutaneous absorptive anesthetic. Furthermore, they may as percutaneous absorptive anesthetic. Furthermore, they may be formed in the form of liquid as spray agent or lotions.

BEST MODE FOR CARRYING OUT THE INVENTION

Figure 1:
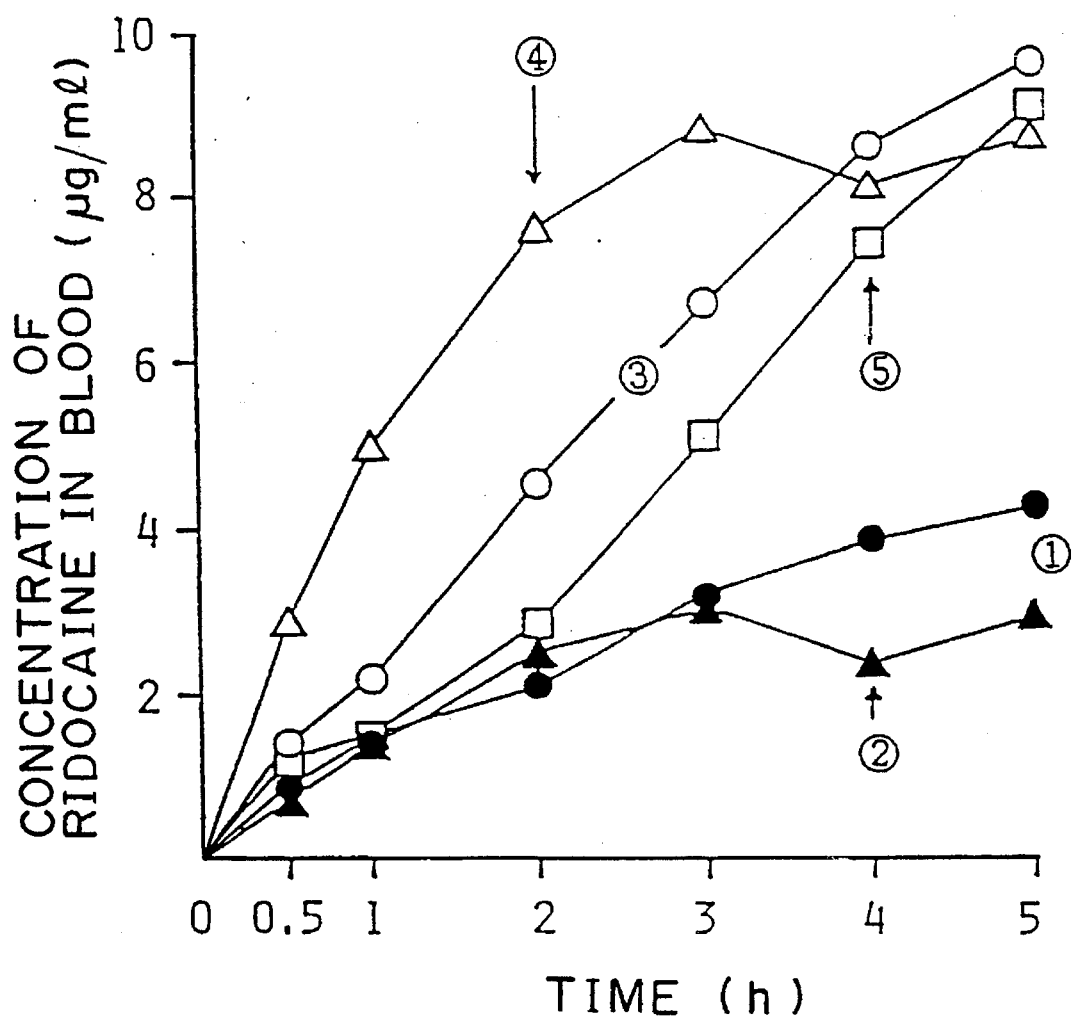
FIG. 1 is a view showing the results of experiment which was carried out using the animal to confirm the effect of percutaneous absorptive anesthetic of the present invention.

Several examples of producing the percutaneous absorptive anesthetic will be described hereinbelow.

EXAMPLE 1

Ointment for Topical Anesthesia

| | |
|---|---|
| Lidocaine | 10 g |
| Compound 4 | 3 g |
| Propylene glycol | 10 g |
| Ethyl alcohol | 30 g |
| Water | 45 g |
| Polyacrylic acid | 1 g |
| Di-isopropanolamine | 1 g |
| Total quantity | 100 g |

The above-described compound was formed into an aqueous ointment in accordance with a standard preparing process. A stabilizing agent and a preservative etc. may be added as needed.

EXAMPLE 2

Production of Cream for Topical Anesthesia

| | |
|---|---|
| Lidocaine base | 10 g |
| Ethanol | 1 ml |
| POE(2) lauryl ether | 9 g |
| Carbopol 934-P | 1 g |
| Compound 4 | 1 g |
| Distilled water | 89 ml |

To produce a cream for topical anesthesia in accordance with the above-described prescription, 10 g of the lidocaine base was first wetted by means of 1 ml ethanol, and the POE(2) lauryl ether was added, followed by heating to elevate the temperature to the level of about 60° C.

On the other hand, Carbopol 934-P was gradually added to the 70 ml distilled water in fragments and the solution was intensely agitated for homogenization.

The compound 4 was dissolved in the remaining 18 ml distilled water.

Then, the suspended solution of the above-described Carbopol 934-P was added into the above-described lidocaine base POE(2) lauryl ether solution in the water of about 60° C., and the solution was agitated by means of glass-rod.

Finally, when the aqueous solution of the compound 4 is added while applying heat, a cream-like product with homogenous property is produced. By cooling the product to a room temperature while agitating it by means of glass-rod, 10% lidocaine cream may be produced which contains the compound 4 in the percentage of one.

The experimental results of the percutaneous absorptive anesthetic in accordance with the present invention will be given below.

[Experiment 1]

(1) Experimental Animal
· Wistar rat (2) Specimen a. Aqueous gel ointment containing 2% of lidocaine.

b. Aqueous gel ointment containing 10% of lidocaine.

c. Aqueous gel ointment in (b) containing 3% of compound 4.

d. Aqueous gel ointment in (a) containing 3% of compound 3.

e. Aqueous gel ointment in (a) containing 3% of compound 4.

f. Aqueous gel ointment in (a) containing 3% of compound 5.

g. Aqueous gel ointment in (a) containing 3% of compound 6.

h. Aqueous gel ointment in (a) containing 3% of compound 7.

(They will be referred to as ointments a, b, c . . . h hereinafter)

(3) Experimental Procedure

The Wistar rats (each of which has an approximate weight of 300 g) were fixed on its back under the urethane anesthesia, and an ointment was applied over an abdomen of the rat body from which a hair had been removed, and the rats were separated into the following groups.

Group with an ointment a applied.

Group with an ointment e applied.

Group with an ointment b applied.

Group with an ointment c applied.

Group with 3% Azone (Trademark registered)—10% lidocaine aqueous gel-ointment applied.

These groups (referred to as the groups 1–5 hereinafter) had an ointment applied in the quantity of 1 g/20 cm$^2$ respectively, and there were 3–5 rats in each one group.

In these groups, the rats had their body portion covered with a polyethylene food wrapping sheet at an area where an ointment was applied, and sealed by means of transparent tape.

Then, a blood was withdrawn through a cannula which had been inserted into the carotid. The blood was pretreated with a heparin and separated by means of centrifugal separator to obtain blood plasma. A fluorescence polarization immunoassay was used to determine the concentration of the lidocaine in the blood. The single figure shows the results of experiment which was performed using the animal. This sole figure shows the profile of the blood concentration up to five hours after the ointment was applied.

In the groups 1 and 2, any significant result was not observed in the blood concentration at any instance, irrespectively whether the compound 4 was contained or not.

However, in the groups 3–5 wherein the concentration of lidocaine was 10%, an absorption promoting effect of the compound 4 was acknowledged.

On the other hand, in the group 5 wherein Azone, known as a percutaneous absorption promoter was added at the rate of 3%, no major effect of improving absorption was found.

EXAMPLE 2

(1) Experimental Subject

Healthy adult.

(2) Specimen

Same as that in the experimental example 1.

(3) Experimental Procedure a. Preparatory Experiment

A preparatory experiment was carried out to verify the skin anesthesia effect of various lidocaine aqueous gel-ointments when they are applied in the quantity of 0.3 g/4 $cm^2$.

Pinprick test was carried out to compare results utilizing lidocaine aqueous gel-ointment which was prepared by mixing the ointments d–h, Xylocaine Jelly (Trademark registered, containing 2% lidocaine, made by Fujisawa Pharmaceutical Co., Ltd.), Azone, a known percutaneous absorption promoter, sodium caprate (to be indicated as Cap Na hereinafter) and isopropyl myristate (to be indicated as IPM hereinafter).

(Criterion)

The skin over which various ointments were applied was pierced several times using a 26 gauge intradermal needle at the time of 1, 1.5, 2, 3 and 4 hours after the application, and the degree of pain felt by the adult was evaluated according to a criterion given below.

++ No pain felt at the area where the ointment was applied.

+ Pain felt at some portions.

− Pain felt at that area.

The results are tabulated in Table 1.

TABLE 1

Results of preparatory experiment to confirm skin anesthesia effect with 3% various percutaneous absorption promoter and 2% lidocaine aqueous gel-ointment.

| Percutaneous absorption promoter | 1 h | 1.5 h | 2 h | 3 h | 4 h |
| --- | --- | --- | --- | --- | --- |
| — | − | − | + | ++ | ++ |
| Compound 3 | − | − | ++ | ++ | ++ |
| Compound 4 | − | − | ++ | ++ | ++ |
| Compound 5 | − | − | + | ++ | ++ |
| Compound 6 | − | − | + | ++ | ++ |
| Compound 7 | − | + | ++ | ++ | ++ |
| Azone | − | − | + | ++ | ++ |
| IPM | − | − | − | ++ | ++ |
| Cap Na | − | + | ++ | ++ | ++ |
| Xylocaine Jelly | − | − | − | − | − |

++ No pain felt at the area where the ointment was applied.

TABLE 1-continued

Results of preparatory experiment to confirm skin anesthesia effect with 3% various percutaneous absorption promoter and 2% lidocaine aqueous gel-ointment.

| Percutaneous absorption promoter | 1 h | 1.5 h | 2 h | 3 h | 4 h |
| --- | --- | --- | --- | --- | --- |

+ Pain felt at some portions.
− Pain felt at that area.

Compounds 3, 4 and 7 began to provide the effect of the skin anesthesia at 1.5 hours after the ointment was applied, and they caused a complete skin anesthesia at 2 hours after the application. Compounds 5 and 6 might provide a skin anesthesia effect substantially equal to that by Azone, and it was found that glycyrrhetic acid derivatives had a percutaneous absorption promoting effect. Xylocaine Jelly exhibited no effect of the skin anesthesia even when 4 hours had passed after its application.

b. Skin Anesthesia Effect

Then, 0.3 g of ointment e was absorbed into a sponge of 25 mm in diameter, and 1 mm in thickness and then the sponge was applied on the internal skin of the forearm of the human. Then a transparent tape was applied for sealing, and pinprick procedure was used to determine the effect of the skin anesthisia. The topical reactions taking place on the skin in the form of redness, edema and blister, etc. were also determined.

(Criterion)

By piercing the 26 gauge intradermal needle through five portions where ointment was to be applied, and the total pain scores of these five portions were indicated with the rule of following scoring.

| No pain | 0 point |
| --- | --- |
| Felt slightly painful | 0.5 point |
| Completely ineffective | 1 point |

In the case of zero point, one portion was selected, and that skin was pierced with the tip end of the needle about 1.0 mm deep so as to confirm the degree of the pain felt at deeper area. In this case, following standards were employed.

No pain ○

Painful ×

A student paired t-test (one side verification) procedure was used to verify a significance of pain score obtained between the pain score 5.0 before the sponge was applied, and that (mean value+standard deviation) at predetermined times respectively after the sponge was applied.

Its results are given in Table 2.

TABLE 2

Pain score with ointment e applied on the forearm of healthy adults.

| Case | | | Time(h) after application | | | | | Time after removal |
| --- | --- | --- | --- | --- | --- | --- | --- | --- |
| No. | Age | Sex | 0.5 | 1 | 1.5 | 2 | 3 | 0.5 h |
| 1 | 27 | M | 3.0 | 2.5 | 2.0 | 2.0 | 1.0 | 0△ |
| 2 | 32 | M | 2.5 | 5.0 | 0△ | 0○ | 0○ | 0○ |
| 3 | 25 | M | 4.0 | 3.5 | 0△ | 0○ | 0○ | 0△ |
| 4 | 25 | M | 5.0 | 0△ | 1.5 | 0○ | 0○ | 0△ |

TABLE 2-continued

Pain score with ointment c applied on the forearm of healthy adults.

| | | | | | | | | |
|---|---|---|---|---|---|---|---|---|
| 5 | 30 | M | 5.0 | 0.5 | 1.5 | 1.0 | 0○ | 0○ |
| 6 | 44 | M | 5.0 | 0△ | 2.0 | 1.0 | 0△ | 2.0 |
| 7 | 30 | F | 4.5 | 2.0 | 3.0 | 2.0 | 0△ | 1.5 |
| 8 | 35 | M | 5.0 | 3.0 | 0△ | 0△ | 0○ | 0△ |
| 9 | 25 | M | 4.0 | 2.0 | 2.5 | 1.5 | 0○ | 0○ |
| 10 | 32 | M | 2.0 | 5.0 | 0○ | 0○ | 0○ | 0○ |
| 11 | 32 | M | 3.0 | 3.0 | 2.0 | 2.0 | 0.5 | 1.0 |
| 12 | 34 | M | 4.5 | 2.0 | 1.0 | 0.5 | 0○ | 2.0 |
| Mean value ± Standard deviation | | | *§ 4.0 ± 1.0 | § 2.2 ± 1.6 | § 1.3 ± 1.0 | *§ 0.8 ± 0.8 | **§ 1.0 ± 0.3 | § 0.5 ± 0.8 |

*: $p < 0.05$,
**: $p < 0.01$, Significantly different from an immediately preceding pain score.
§: $<0.01$, Significantly different from pain score (5.0) before application.

The mean pain score was decreased significantly such that it was 4.0±1.0 at 0.5 hours, 2.2±1.6 at one hour, 1.3±1 at 1.5 hour, 0.8±0.8 at 2 hours and 0.1±0.3 at three hours after application. At 3 hours after the ointment was applied, 8 of 12 persons (67%) felt no pain when the 26 gauge intradermal needle was pierced into the skin about 1 mm deep vertically. At 0.5 hour after the removal of aqueous gel ointment applied, the pain score was 0.5±0.8 which was not so significant, but a pain was already felt. As for the topical reaction occurring on the skin where the ointment was applied, 3 persons (25%) had a slight redness, but had no whiteness, edema and blister etc. No complaint about anesthesia was reported. The skin redness was disappeared within 1 hour after the ointment was applied.

EXAMPLE 3

(1) Experimental Subject

A patient who was to receive an operation.

(2) Specimen

Same as those in the example 1.

(3) Experimental Procedure

The ointment c into which the compound 4 was added, and the reference ointment b into which no compound 4 was added were absorbed in the quantity of 0.3 g to the sponge having dimensions of 25 mm diameter and 1 mm thickness. The sponge was applied over an area in which the vein is punctured in accordance with a double-blind assay method. The area was sealed off with a transparent tape, and the topical reaction and the painless effect occurring on the skin were compared about 1 hour later.

(4) Criterion

The following pain score was employed as a criterion.

| | |
|---|---|
| No pain felt at all 5 points | 0 point |
| Pain felt only at 2 points | 2 point |
| Pain felt at 3 points and slight pain felt at further 1 point | 3.5 point |

When the pain score was zero, the needle was pierced into the skin about 1.0 mm deep to verify the pain.

The results are given in Table 3.

TABLE 3

Improving effect of compound 4 which affects pain score (PS) in accordance with pinprick procedure.

| Ointment Group c | | Ointment Group b | |
|---|---|---|---|
| (Case No.) | (PS) | (Case No.) | (PS) |
| 1 | 0 | 13 | 3 |
| 2 | 3 | 14 | 3 |
| 3 | 1 | 15 | 4 |
| 4 | 2 | 16 | 5 |
| 5 | 1 | 17 | 2 |
| 6 | 5 | 18 | 1 |
| 7 | 0 | 19 | 0 |
| 8 | 0 | 20 | 0.5 |
| 9 | 1 | 21 | 3 |
| 10 | 0 | 22 | 5 |
| 11 | 2 | 23 | 1 |
| 12 | 0.5 | 24 | 2 |
| Mean ± SD | 1.3 ± 1.5* | Mean ± SD | 2.5 ± 1.7* |

*: $p < 0.05$, Difference between two groups is significant.

The ointment group c in which the compound 4 was added had the pain score of 1.3±1.5 and the ointment group b into which the compound 4 was not added showed 2.5±1.7, indicating that the compound 4 was effective in removing the pain of the skin ($p<0.05$). Those who marked the zero point in the pain score were 4 persons from the ointment group c and 1 person from the ointment group b. Among these 5 persons, 3 of 4 persons from the ointment group c and 1 person from the ointment group b had experienced no pain, even when the 26 gauze intradermal needle was pierced into the skin about 1 mm deep. Those whose pain score was less than 1 point when measured in accordance with pinprick procedure were 8 persons from the ointment group c and 4 persons from the ointment group b. With these 12 patients, intravenous dwell needle was directly pierced. In this case, veintravenous injection was carried out through the 20–18 gauge dwell needle instead of the 0.5% procaine hydrochloride intradermal syringe which would normally performed to the vein piercing portion. The pain caused by piercing the needle through the skin and into the vein was evaluated with the pain score which was classified into five ranks.

| | |
|---|---|
| No pain felt | 0 point |
| Felt contact with something with no pain | 1 point |
| Felt slightly painful | 2 point |
| Felt painful | 3 point |
| Very painful | 4 point |

Wilcoxon verification was employed to verify a difference in significance, and Student t-test was used for other purposes.

In all cases, it was verified that there was a difference in significance, when the dangerous factor was less than 5%. The results are given in Table 4.

TABLE 4

Pain Score (PS) when the skin and the vein are pierced with in-vena dwell needle.

| Ointment group c | | | Ointment group b | | |
|---|---|---|---|---|---|
| (Case No.) | (A) | (B) | (Case No.) | (A) | (B) |
| 1 | 1 | 1 | 18 | 3 | 4 |
| 3 | 3 | 2 | 19 | 1 | 2 |
| 5 | 3 | 4 | 20 | 2 | 3 |
| 7 | 3 | 3 | 23 | 1 | 4 |
| 8 | 1 | 1 | n = 4 | 1.8 ± 1.0* | 3.3 ± 1.0*§ |
| 9 | 1 | 1 | | | |
| 10 | 1 | 1 | | | |
| 12 | 3 | 2 | | | |
| n = 8 | 2.0 ± 1.1 | 1.9 ± 1.12§ | | | |

(A): PS when the skin is pierced.
(B): PS when the vena is pierced.

The pain score when the skin was pierced was 2.0±1.1 with the ointment group c, and 1.8±1.0 with the ointment group b, indicating no significant difference between these groups. On the other hand, the pain score when the vein was pierced was 1.9±1.1 with the ointment group c, and 3.3±1.0 with the ointment group b, indicating that the ointment group c had a significantly lower pain score (P<0.05).

The results of acute toxic examination (LD50) which was carried out with the rat through the oral dose of the compound were follows.

Compound 3: 520 mg/kg

Compound 4: 1,320 mg/kg

Compound 5: 1,257–1,520 mg/kg

Compound 6: 1,283–1,499 mg/kg

Compound 7: 628–793 mg/kg

Industrial Applicability

It was verified in the above experimental example that the percutaneous absorption of lidocaine was facilitated through glycyrrhetic acid derivatives and the pain was removed at the time of skin anesthesia and vein piercing. This means that the compound is effective not only to the vein fixing, epidural anesthesia and spinal anesthesia etc. in the field of anesthetist, but also effective to children who have a fear of syringe.

In the field of anesthesia, when the skin is not treated with an anesthetic, the patient may be released from pain and the surgeon may concentrate his/her attention to the treatment, if the compound is applied over the skin beforehand.

Thus, the present invention may promise an extensive application for clinical purposes.

We claim:

1. A percutaneous absorptive anesthetic composition comprising:
one or more compounds selected from the group consisting of:
glycyrrhetic acid 3β-monohemisuccinate;
glycyrrhetic acid 3β-monohemiphthalate;
18β-olean-12-ene-3 β,30-diol-3 β,30-dihemiphthalate;
18β-olean-9(11),12-diene-3 β,30-diol-3 β,30-dihemiphthalate;
olean-11,13(18)-diene-3 β,30-diol-3 β,30-dihemiphthalate;
and a pharmaceutically allowable salt of any of the foregoing, and an anesthetic.

2. The percutaneous absorptive anesthetic composition as claimed in claim 1, wherein said anesthetic is selected from the group consisting of lidocaine, bupivacaine, tetracaine and prilocaine.

3. The percutaneous absorptive anesthetic composition as claimed in any one of claims 1 or 2, wherein said one or more compounds are about 0.1–20 percent of said composition by weight, and said anesthetic is about 0.1–50 percent of said composition by weight.

4. A percutaneous absorptive anesthetic composition comprising:
glycyrrhetic acid 3β-monohemiphthalate or a pharmaceutically allowable salt thereof; and
an anesthetic.

5. A method for alleviating pain caused by piercing skin of a mammal, comprising:
applying to the skin to be pierced a percutaneous absorptive anesthetic composition comprising an anesthetic and one or more compounds selected from the group consisting of:
glycyrrhetic acid 3β-monohemisuccinate;
glycyrrhetic acid 3β-monohemiphthalate;
18β-olean-12-ene-3 β,30-diol-3 β,30-dihemiphthalate;
18β-olean-9(11),12-diene-3 β,30-diol-3 β,30-dihemiphthalate;
olean-11,13(18)-diene-3 β,30-diol-3 β,30-dihemiphthalate glycyrrhetic acid; and
a pharmaceutically allowable salt of any of the foregoing; and piercing the skin of the mammal.

6. A method for alleviating pain according to claim 5, wherein said anesthetic is selected from the group consisting of lidocaine, bupivacaine, tetracaine and prilocaine.

7. A method for alleviating pain according to claim 5, wherein the piercing step comprises piercing with a needle.

8. A method for alleviating pain caused by piercing skin of a mammal, comprising:
applying to the skin to be pierced a percutaneous absorptive anesthetic composition comprising an anesthetic, and glycyrrhetic acid 3β-monohemiphthalate or a pharmaceutically allowable salt thereof; and
piercing the skin of the mammal.

* * * * *